United States Patent [19]
Williams et al.

[11] Patent Number: 5,852,222
[45] Date of Patent: Dec. 22, 1998

[54] PROCESS

[75] Inventors: Alfred Glyn Williams, Binfield; Martin Charles Bowden, Brighouse; Stephen Martin Brown, Cumberworth, all of United Kingdom

[73] Assignee: Zeneca Limited, London, England

[21] Appl. No.: 706,948

[22] Filed: Sep. 3, 1996

[30] Foreign Application Priority Data

Sep. 11, 1995 [GB] United Kingdom ................... 9518525

[51] Int. Cl.$^6$ ................................................ C07C 19/02
[52] U.S. Cl. ............................................. 570/134; 570/169
[58] Field of Search ..................... 570/134, 169

[56] References Cited

U.S. PATENT DOCUMENTS

| | | | |
|---|---|---|---|
| 2,398,181 | 4/1946 | Johnson | 570/134 |
| 2,551,573 | 5/1951 | Downing et al. | 570/134 |
| 2,554,857 | 5/1951 | Gochenour | 570/169 |
| 4,980,324 | 12/1990 | Kellner et al. | 570/134 X |
| 5,032,648 | 7/1991 | Nicholas. | |
| 5,146,015 | 9/1992 | Li. | |
| 5,316,690 | 5/1994 | Li | 570/134 X |

FOREIGN PATENT DOCUMENTS

| | | |
|---|---|---|
| 699649 | 3/1996 | European Pat. Off. . |
| 1156771 | 11/1963 | Germany . |

*Primary Examiner*—Paul F. Shaver
*Attorney, Agent, or Firm*—Joel G. Ackerman

[57] ABSTRACT

The present invention provides the novel chlorofluorohydrocarbon 1,1-difluoro-1,4-dichlorobutane, and a process for its preparation by reacting 1,1,1,4-tetrachlorobutane with hydrogen fluoride in the liquid phase. The product has useful solvent properties and is also useful in synthetic chemistry for the introduction of fluorocarbon functionality.

10 Claims, No Drawings

PROCESS

The present invention relates a novel chlorofluorohydrocarbon and to a process for its preparation. More particularly it relates to 1,1-difluoro-1,4-dichlorobutane and a process for preparing it from the known compound 1,1,1,4-tetrachlorobutane.

Accordingly the present invention provides 1,1-difluoro-1,4-dichlorobutane. In a further aspect the present invention provides a process for preparing 1,1-difluoro-1,4-dichlorobutane comprising reacting 1,1,1,4-tetrachlorobutane with hydrogen fluoride in the liquid phase.

The process of the present invention is illustrated by the following reaction scheme:

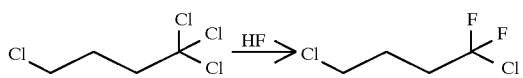

The reaction is conveniently conducted in a vessel whose lining is resistant to corrosion by chemical reaction with hydrogen fluoride, such as for example, one made from "Hastalloy" (Registered Trade Mark) or Monel metal.

The reaction can conveniently be carried out in the presence of a catalyst such as a polyvalent metal halide. Examples of suitable catalysts include ferric chloride, particularly in the presence of activated charcoal, aluminium fluoride, aluminium oxide (γ-alumina), chromium fluoride, manganese difluoride, ferric fluoride, cobalt dichloride, nickel difluoride, zirconium fluoride, thorium fluoride, oxyfluorides and antimony pentachloride, particularly in the presence of activated charcoal.

Tin halides are preferred catalysts and a particularly useful catalyst is tin (IV) chloride.

The reaction temperature is preferably within the range 50° to 10° C., and more preferably within the range 70° to 90° C. The duration of the reaction is usually within the range 4 to 10 hours.

The reaction is carried out using hydrogen fluoride which is a volatile material having a boiling point under normal atmospheric pressure of 19.5° C. In order to conduct the reaction in the liquid phase a sealed reaction vessel may be used in which the reaction proceeds under the autogenic pressure of the reactants and products. In a preferred variant of this process a vessel can be used which is equipped with means to permit the hydrogen chloride produced during the reaction to to vented, preferably continuously, whilst the reaction is maintained in the liquid phase by the autogenic pressure of the reactants and products. This may be achieved by the use of a condenser which liquifies evaporating hydrogen fluoride whilst permitting the escape of the more volatile hydrogen chloride gas. Such an arrangement permits the autogenic pressure to be maintained in the range of about 175 to about 230 psig (about 12 to about 16 bar).

The product mixture consists principally of the desired 1,1-difluoro-1,4-dichlorobutane, with minor quanties of other materials present, particularly 1,1,1-trifluoro-4-chlorobutane. When the reaction is conducted under a temperature of 85° to 90° C. with venting of the hydrogen chloride over a 6 to 7 hour period good yields and conversion rates may be obtained with minimal co-production of the 1,1,1-trifluoro-4-chlorobutane. Isolation of the desired product can be achieved readily by fractional distillation.

1,1-difluoro-1,4,-dichlorobutane is a novel compound which has useful properties as a solvent, and may be used, for example, in degreasing electrical and electronic components such as printed circuits and the like. Because of its higher boiling point and lower volatility compared with the halomethanes and haloethanes traditionally used for degreasing, and the fact that it is a chlorofluorohydrocarbon and not a chlorofluorocarbon, its use may have environmental advantages. It is also of use as a synthetic chemical intermediate particularly for introducing fluorocarbon functionality into a molecule, for example as a means of introducing the difluorobutenyl group into the nematicidal pyrimidine compounds of International Patent Application no. PCT/GB 93/01912.

Various further preferred features and embodiments of the present invention will now be described with reference to the following non-limiting examples. The following abbreviations are used: NMR=nuclear magnetic resonance; s=singlet; d=doublet; dd=double doublet; t=triplet; q=quartet; m=multiplet; br=broad; M=mole; mM=millimoles; $CDCl_3$=deuteriochloroform. Chemical shifts (δ) are measured in parts per million from tetramethylsilane. $CDCl_3$ was used as solvent for NMR spectra unless otherwise stated.

EXAMPLE 1

5 g 1,1,1,4-Tetrachlorobutane (25 mmoles) was charged to a 25 ml Monel autoclave, which was then purged. Hydrogen fluoride 10.6 g (535 mmoles) was added as a liquified gas, the stirrer started and the vessel heated to 80° C. at a ramp rate of 1 deg/min where it was stirred for 18 hours by which time the pressure had increased to 298 psi. The heating was turned off to allow the reaction to cool to room temperature. After the temperature had dropped to ca. 20° C. the vessel was cooled in an ice/IMS bath and the excess pressure (154 psi at room temperature) vented via a stirred water trap keeping the internal temperature >0° C. to reduce the loss of entrained volatile products. On completion of the venting the vessel was opened and the dark red reaction mixture was poured carefully onto ice (ca. 50 gms), the organic phase separated, small amounts of sodium fluoride and magnesium sulphate were added to absorb any hydrogen fluoride and water. The weight of this liquid before the addition of the $NaF/MgSO_4$ was 1.7 gms. The aqueous liquors were extracted with dichlorobenzene (2×30 mls) and the extracts backwashed with water and dried over magnesium sulphate.

Analysis: Analysis by GC (gas chromatography) of the recovered 1.7 g of sample indicated: 0% starting material, 11% 1-fluoro-1,1,4-trichlorobutane, 57% 1,1-difluoro-1,4-dichlorobutane (desired product).

$^1$Hnmr ($CDCl_3$): 2.15 (m, 2H, $CH_2$); 2.50 (m, 2H, $CH_2CF_2Cl$); 3.55 (br t, 2H, $CH_2Cl$).

MS: 142 ($M^+$–HF), 127 ($M^+$–Cl).

EXAMPLE 2

5.5 g 1,1,4-Tetrachlorobutane (28 mmoles) was charged to a 25 ml Monel autoclave, which was then purged. Hydrogen fluoride 10.1 g (505 mmoles) was added as a liquified gas the stirrer started and the vessel heated to 30° C. at a ramp rate of 1 deg/min. The initial pressure at this temperature was 27 psi, this rose to 36 psi while the reaction was stirred overnight. This rate of pressure increase was not considered to be sufficient so the reaction temperature was increased to 50° C. and the reaction stirred for a further 23 hours while the pressure increased from 47 psi to 106 psi. The vessel was cooled in an ice/IMS bath and the excess pressure (72 psi at room temperature) vented via a stirred water trap keeping the internal temperature <0° C. to reduce the loss of entrained volatile products. On completion of the venting the vessel was opened and the dark red reaction mixture was poured carefully onto ice (ca. 50 gms) and the organic phase separated, small amounts of sodium fluoride and magnesium sulphate were added to the straw coloured liquid to absorb any hydrogen fluoride and water. The damp weight of the material was 2.85 g. The aqueous liquors were extracted with with dichlorobenzene (2×30 mls) and the extracts backwashed with water and dried over magnesium sulphate. GC analysis indicated the presence 1,1-difluoro-1,4-dichlorobutane.

EXAMPLE 3

4.9 g 1,1,1,4-Tetrachlorobutane (25 mmoles) was charged to a 25 ml Monel autoclave, which was then purged. Hydrogen fluoride 10.7 g (535 mmoles) was added as a liquified gas, the stirrer started and the vessel heated to 65° C. at a ramp rate of 1 deg/min. The initial pressure at this temperature was ca. 70 psi, this rose to 184 psi over the next 23 hours. After allowing the temperature to drop to ca. 20° C. the vessel was cooled in an ice/IMS bath and the excess pressure (120 psi at room temperature) vented via a stirred water trap (no indication of carry over into this trap) keeping the internal temperature <0° C. to reduce the loss of entrained volatile products (the weight of the vessel dropped by approx. 1 gm during this process). On completion of the venting the vessel was opened and the dark red reaction mixture was poured carefully onto ice (ca 50 gms) and the organic phase separated, small amounts of sodium fluoride and magnesium sulphate were added to the straw coloured liquid to absorb any hydrogen fluoride and water. Damp weight of material was ca. 1 gm. The aqueous liquors were extracted with dichlorobenzene (2×30 mls) and the extracts backwashed with water and dried over magnesium sulphate. GC analysis indicated the presence of the desired product, 1,1-difluoro- 1,4-dichlorobutane.

EXAMPLE 4

2.0 g 1,1,1,4-tetrachlorobutane (10 mmoles) was charged to a 25 ml Monel autoclave, which was then purged. Hydrogen fluoride 9.8 g (490 mmoles) was added as a liquified gas, the stirrer started and the vessel heated to 80° C. at a ramp rate of 1 deg/min. The initial pressure at this temperature was 113 psi, this rose to 161 psi over the next 2 hours 20 minutes before the reaction was left to stir overnight, still at 80° C. The heating was discontinued and the reaction allowed to cool to room temperature. The vessel was cooled in an ice/IMS bath and the excess pressure (78 psi at room temperature) vented via a caustic scrubber keeping the internal temperature <0° C. to reduce the loss of entrained volatile products. On completion of the venting the vessel was opened and the dark red reaction mixture was poured carefully onto ice (ca. 50 gms) and the organic phase extracted into dichloromethane (3×15 mls). The extracts were analysed by GC which suggested that there were two major products (>5% level) with no starting material left. The extracts were dried over magnesium sulphate and the dichloromethane distilled off at atmospheric pressure to give 1.76 g of a dark liquid.

GC analysis indicated that the recovered sample contained 36% of the desired product, 1,1-difluoro-1,4-dichlorobutane.

EXAMPLE 5

This Example illustrates the preparation of 1,1-difluoro-1,4-dichlorobutane in the presence of tin (IV) chloride.

1,1,1,4-Tetrachlorobutane (35.3 g), liquified hydrogen fluoride (20.5 g) and tin(IV) chloride (2.6 ml) were charged sequentially at −20° C. into a Monel autoclave fitted with a metal condenser cooled to −15° C. topped with a needle valve to permit venting of gases. The autoclave temperature was raised to 90° C. at ramp rate of 2° C. and maintained at this temperature for 4 hours with periodic venting of the hydrogen chloride produced so as to maintain the internal pressure within the range 180 to 220 psi. The autoclave was then cooled to −10° C. and the contents aded carefully to ice (50 g). After allowing the ice to melt the mixture was extracted with dichloromethane (2×20 ml), the extracts combined and dried over sodium fluoride and magnesium sulphate, and the product mixture recovered by evaporation of solvent. Gas chromatographic analysis indicated the presence of a mixture of ca. 79% of the desired 1,1-difluoro-1,4-dichlorobutane and 18% of 1,1,1-trifluoro-4-chlorobutane. The 1,1-difluoro-1,4-dichlorobutane was separated by fractional distillation and obtained as a colourless liquid (20.74 g, b.p 63°–65° C. at 138 mbar).

We claim:

1. 1,1-Difluoro-1,4-dichlorobutane.

2. A process for preparing 1,1-difluoro-1,4-dichlorobutane comprising reacting 1,1,1,4-tetrachlorobutane with hydrogen fluoride in the liquid phase under autogenic pressure.

3. A process according to claim 2 carried out in the presence of a catalyst selected from polyvalent metal halides and aluminium oxides.

4. A process according to claim 3 wherein the metal halide is selected from ferric chloride, aluminium fluoride, chromium fluoride, manganese difluoride, ferric fluoride, cobalt dichloride, nickel difluoride, zirconium fluoride, thorium fluoride, oxyfluorides and antimony pentachloride, optionally in the presence of activated charcoal.

5. A process according to claim 2 wherein the metal halide is selected from tin halides.

6. A process according to claim 5 wherein the tin halide is tin(IV) chloride.

7. A process according to claim 2 carried out at a temperature within the range 50° to 100° C.

8. A process according to claim 2 carried out under autogenic pressure in a closed vessel.

9. A process according to claim 2 carried out under autogenic pressure in a vessel permitting continuous venting of hydrogen chloride gas produced by the reaction.

10. A process according to claim 9 in which the autogenic pressure is maintained within the range of about 175 to about 230 psig (about 12 to about 16 bar).

* * * * *